United States Patent [19]

Leeke et al.

[11] 4,336,036
[45] Jun. 22, 1982

[54] FILTER AND METHOD OF MAKING SAME

[75] Inventors: Gordon Leeke, Glastonbury; Timothy Webster, New Britain, both of Conn.

[73] Assignee: AMF Incorporated, White Plains, N.Y.

[21] Appl. No.: 223,458

[22] Filed: Jan. 8, 1981

[51] Int. Cl.³ ............................................. B01D 19/00
[52] U.S. Cl. ................................. 55/159; 128/214 R; 210/94
[58] Field of Search ............. 55/158, 159; 128/214 R, 128/214 C, 214.2; 210/94, 136, 321.1, 446

[56] References Cited

U.S. PATENT DOCUMENTS

| | | | |
|---|---|---|---|
| 3,523,408 | 8/1970 | Rosenberg | 55/159 |
| 3,631,654 | 1/1972 | Riely et al. | 55/159 |
| 3,650,093 | 3/1972 | Rosenberg | 55/159 |
| 3,778,971 | 12/1973 | Granger et al. | 55/159 |
| 3,803,810 | 4/1974 | Rosenberg | 55/159 |
| 3,834,124 | 9/1974 | Ichikawa | 55/159 |
| 3,905,905 | 9/1975 | O'Leary et al. | 55/159 X |
| 4,004,587 | 1/1977 | Jess | 55/159 X |
| 4,009,714 | 3/1977 | Hammer | 128/214 C X |
| 4,030,495 | 6/1977 | Virag | 128/214.2 |
| 4,031,891 | 6/1977 | Jess | 128/214.2 X |
| 4,035,304 | 7/1977 | Watanabe | 128/214.2 X |
| 4,066,556 | 1/1978 | Vaillancourt | 128/214 R X |
| 4,113,627 | 9/1978 | Leason | 128/214 R X |
| 4,177,149 | 12/1979 | Rosenberg | 55/159 X |
| 4,188,948 | 2/1980 | Swinton | 55/159 X |
| 4,190,426 | 2/1980 | Ruschke | 128/214 R X |
| 4,276,170 | 6/1981 | Vaillancourt | 55/159 X |
| 4,278,084 | 7/1981 | Pope, Jr. | 55/159 X |

*Primary Examiner*—Robert H. Spitzer
*Attorney, Agent, or Firm*—David E. Dougherty; Charles J. Worth

[57] ABSTRACT

A deformable liquid filter with means for purging air and gases having a housing with spaced flexible walls and a hydrophilic membrane defining a collapsible inlet chamber with air and gas vent means on one side of the membrane and an outlet chamber on the opposite side of the membrane with membrane support means which prevents the outlet chamber from collapsing.

6 Claims, 3 Drawing Figures

FILTER AND METHOD OF MAKING SAME

This invention relates to membrane type filters particularly adapted to remove gases and minute contaminants from intravenous liquids and the method of making the same.

Liquid/gas separating means are well known in the art and filters for removing gases entrained in liquids have found general acceptance in various environments and particularly in the medical and pharmaceutical areas. In medical applications such as intravenous administration of liquids, the requirements and demands upon the apparatus are severe. Therefore, it is obvious that filters incorporated in apparatus for intravenous administration must be sealed and capable of being sterilized in addition to providing absolute removal of gases from the intravenous liquid while permitting uninterrupted flow of the total liquid provided at the source to the patient. This low pressure filter must be capable of being taped to a patient's arm without causing undue discomfort or otherwise supported against movement which could be transmitted to a catheter.

One basic problem encountered with intravenous filters is the difficulty in starting the flow of liquid therethrough. This generally is caused by air initially within the filter which tends to block wetting of the membrane. One means presently available to positively remove gases from a filter is by use of a syringe as disclosed by U.S. Pat. No. 4,188,948 to J. A. Swinton. The filter unit in accordance with this concept requires the additional structure of a non-pierceable adapter with a resealable diaphragm. Also, extraneous equipment, such as the syringe, is required, and piercing the diaphragm could possibly create a source of contamination of the sterile area within the filter. Two impositive means relying on the low pressure within an intravenous filter for dispelling gases are provided by U.S. Pat. No. 3,803,810 to D. J. Rosenberg which discloses the use of a hydrophobic membrane covered vent, and U.S. Pat. No. 4,190,426 to R. R. Ruschke which provides a valved vent.

Accordingly, an object of the present invention is to provide an improved filter for intravenous administration of fluids which is relatively small in size, light in weight and inexpensive to manufacture.

Another object of the present invention is to provide the foregoing filter which is deformable and can be taped to a patient's arm without causing undue discomfort or can be otherwise supported against movement which could be transmitted to a catheter.

And another object of the present invention is to provide the foregoing filter capable of positive purging to remove air or gases from the proximity of the membrane.

And still another object of the present invention is to provide a rapid and inexpensive method of making the foregoing filter.

The foregoing and other objects and advantages will appear more fully hereinafter from a consideration of the detailed description which follows, taken together with the accompanying drawings wherein a single embodiment of the invention is illustrated by way of example. It is to be expressly understood, however, that the drawings are for illustration purposes only and are not to be construed as defining the limits of the invention.

Figure 1:
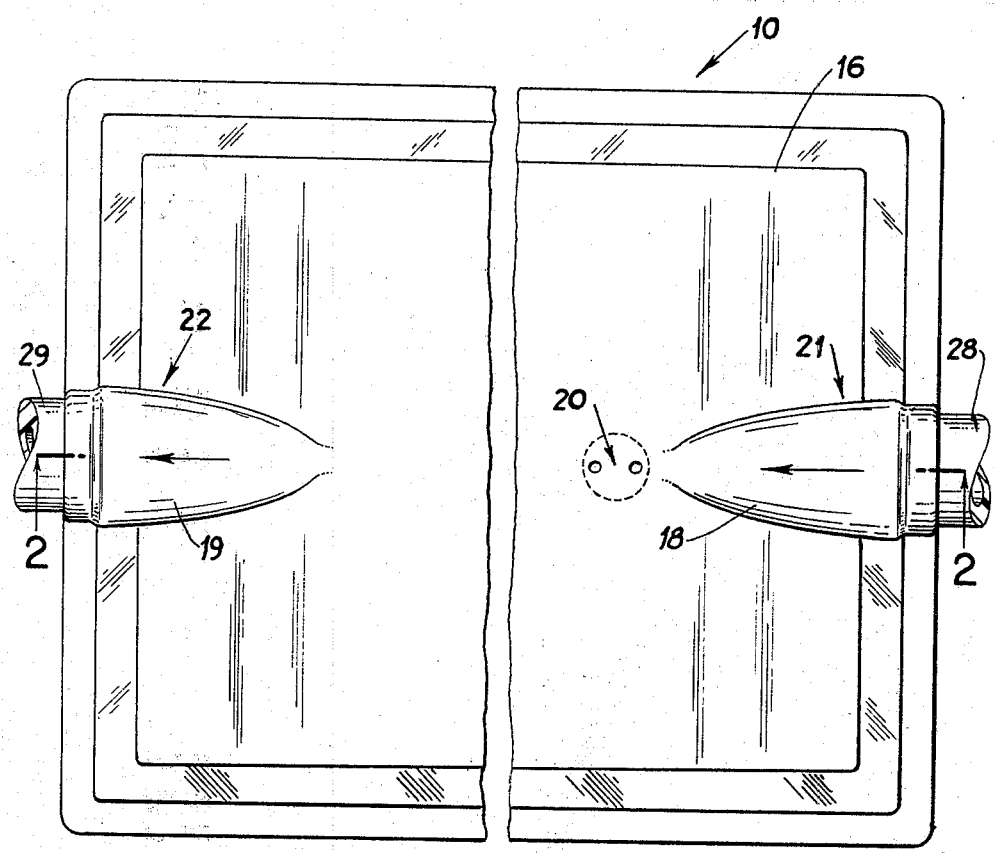
FIG. 1 is a plan view of a filter in accordance with the present invention.
Figure 2:
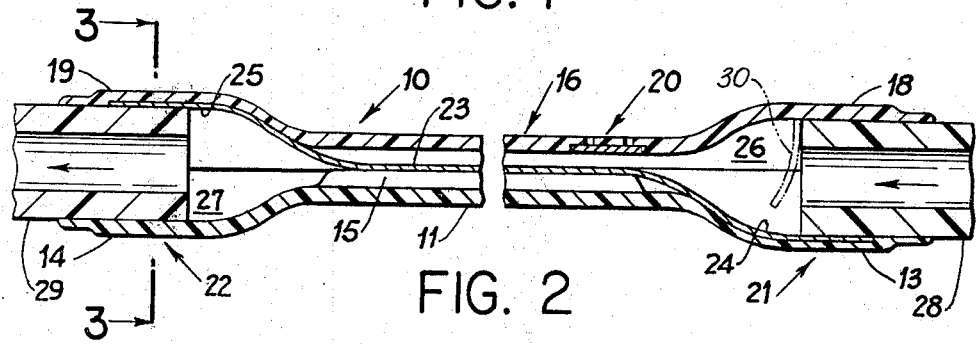
FIG. 2 is a sectional view taken on line 2—2 of FIG. 1.
Figure 3:
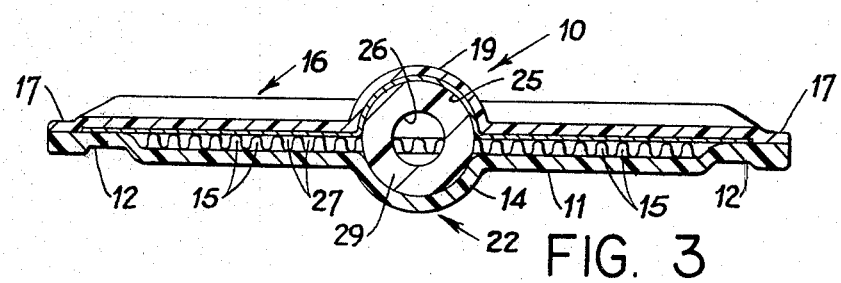
FIG. 3 is a sectional view taken on line 3—3 of FIG. 2.

Referring now to the drawings, a filter in accordance with the present invention has a substantially flat rectangular case or housing 10 provided with an inlet 21 and an outlet 22 disposed at its opposite ends. The case or housing 10 is formed by a flexible lower wall 11 and a flexible upper wall 16 which are equal in size and rectangular shape, and are suitably spaced apart from one another with their respective edges 12 and 17 appropriately sealed or fused together. The opposite ends of the lower wall 11 are provided with semi-circular deformations 13 and 14 which are disposed in face to face alignment and cooperate with similar deformations 18 and 19, respectively, at the ends of the upper wall 16 to define the inlet 21 and the outlet 22.

A membrane 23 is disposed between the lower and upper walls 11 and 16 dividing the interspace into an inlet chamber 26 and an outlet chamber 27. The membrane 23 is a planar with its edges sealed or fused between the edges 12 of the lower wall 11 and the edges 17 of the upper wall 16. The membrane 23 is provided with semicircular deformations 24 and 25 at its opposite ends which extend in opposite directions from the plane of the membrane. Thus, deformation 24 is disposed in contact with the deformation 13 of the lower wall 11 providing communication between the inlet 21 and inlet chamber 26 while blocking flow from the inlet to the outlet chamber 27. Similarly, deformation 25 is disposed in contact with the deformation 19 of the upper wall 16 providing communication from the outlet chamber 27 to the outlet 22 while blocking flow from the inlet chamber 26 to the outlet.

Tubes or tubular nipples 28 and 29 extend into the inlet 21 and outlet 22, respectively. When the edges 12 and 17 are fused or sealed together with the edges of the membrane 23, a sealed connection of the tubular member 28, deformation 24 and inlet 21 is also formed with the deformation 24 sealed between the tubular member 28 and deformation 13. A second sealed connection of the tubular member 29, deformation 25 and the outlet 22 is also formed with the deformation 25 sealed between the member 29 and the deformation 19.

The lower wall 11 also is provided with a laterally spaced series of inwardly disposed ribs 15 which form longitudinal flow paths therebetween from an area adjacent the inlet 21 to an area adjacent the outlet 22. The upper wall 16 is provided with a membrane covered vent 20 for the inlet chamber 26. A no load check or directional valve such as a flap valve 30 may be provided in the inlet 21 or between the inlet and the I.V. source to prevent back flow when the inlet chamber 26 is purged.

The upper and lower walls 16 and 11 are preferably formed of any suitable flexible plastic material such as a polyurethane or polyvinyl chloride sheet or film approximately 0.020 inches thick which will provide the light weight collapsible or compressible housing 10. The membrane 23 is approximately an 0.20 to 0.22 micron filter material of about 0.005 inches in thickness. The membrane 23 may be any suitable hydrophilic membrane available, such as a membrane made in accordance with Marinaccio U.S. Pat. No. 3,876,738 issued Apr. 8, 1975, since it is not subject to high pressure differentials and is supported by the ribs 15 which also prevent the outlet chamber 27 from being collapsed.

However, a charge modified membrane in accordance with Emond et al. application Ser. No. 201,366 filed Oct. 27, 1980 may be preferred while any suitable hydrophobic membrane may be used for the vent 20.

In operation, the novel filter in accordance with the present invention is connected between an I.V. source and a catheter, and being deformable, is thereafter suitably fixed to a patient's arm. Pressure can then be applied to the upper wall 16 tending to collapse the inlet chamber 26 purging air and/or gases through the vent 20. The discharge chamber 27 will not collapse because of the ribs 15, and the directional valve 30 or other such means in the inlet line from the I.V. source prevents back flow of the air and/or gas being purged. Since the vent 20 includes a hydrophobic membrane, only air and/or gas will escape therethrough. On the other hand, membrane 23 being hydrophilic will pass only liquid, entrapping air and/or gas in the inlet chamber 26 to be dispelled through the vent 20.

Although but a single embodiment of the invention has been illustrated and described in detail, it is to be expressly understood that the invention is not limited thereto. Various changes may be made in the design and arrangement of the parts without departing from the spirit and scope of the invention as the same will now be understood by those skilled in the art.

What is claimed is:

1. A deformable liquid filter with means for manually purging air and gases, comprising
    a housing having a pair of flexible walls in spaced apart face to face alignment and sealed together at the edges;
    a hydrophilic membrane in said housing with its edges sealed between said sealed edges dividing the space between said pair of walls into an inlet chamber and an outlet chamber;
    a longitudinally spaced pair of tubular members extending through opposite ends of said housing each communicating with a different one of said chambers and being sealed between the sealed edges of said membrane and a different one of said pair of walls;
    one of said pair of walls having vent means for said inlet chamber and being movable toward said membrane for manually collapsing said inlet chamber urging air and gases to be purged through said vent means; and
    the other of said pair of walls having means supporting said membrane and preventing said outlet chamber from collapsing.

2. A deformable liquid filter in accordance with claim 1, and said vent means comprising
    at least one opening through said one of said pair of walls; and
    a hydrophobic membrane extending across said opening and being adhered to said one of said pair of walls.

3. A deformable liquid filter in accordance with claim 1, and said support means comprising
    a laterally spaced series of longitudinal ribs extending from said other of said pair of walls into said outlet chamber to said membrane.

4. A deformable liquid filter in accordance with claim 3, and said vent means comprising
    at least one opening through said one of said pair of walls; and
    a hydrophobic membrane extending across said opening and being adhered to said one of said pair of walls.

5. A method of making a deformable liquid filter with means for manually purging air and gases, comprising the steps of
    providing a pair of spaced apart flexible walls, one with vent means for air and gases and the other with a laterally spaced series of longitudinal ribs extending toward said one of said walls;
    providing a pair of tubular members each extending across the edges of said membrane and wall at opposite sides thereof
    sealing the edges of said walls together with the edges of said membrane sealed therebetween and simultaneously sealing the edges of said membrane and a different one of said pair of walls to each of said tubular members.

6. A method of making a deformable liquid filter in accordance with claim 5, and further including the preliminary steps of
    making at least one opening through said one of said pair of walls; and
    adhering a hydrophobic membrane to said one of said pair of walls across said opening.

* * * * *